US012661050B2

(12) United States Patent
Fukada et al.

(10) Patent No.: US 12,661,050 B2
(45) Date of Patent: Jun. 23, 2026

(54) BIOELECTRODE AND CAPACITOR

(71) Applicant: NTT, Inc., Tokyo (JP)

(72) Inventors: Kenta Fukada, Tokyo (JP); Suzuyo Inoue, Tokyo (JP); Michiko Seyama, Tokyo (JP)

(73) Assignee: NTT, INC., Tokyo (JP)

( * ) Notice: Subject to any disclaimer, the term of this patent is extended or adjusted under 35 U.S.C. 154(b) by 392 days.

(21) Appl. No.: 18/257,799

(22) PCT Filed: Dec. 16, 2020

(86) PCT No.: PCT/JP2020/046941
§ 371 (c)(1),
(2) Date: Jun. 15, 2023

(87) PCT Pub. No.: WO2022/130531
PCT Pub. Date: Jun. 23, 2022

(65) Prior Publication Data
US 2024/0108269 A1 Apr. 4, 2024

(51) Int. Cl.
*A61B 5/263* (2021.01)
*A61B 5/07* (2006.01)
*A61B 5/277* (2021.01)

(52) U.S. Cl.
CPC ............... *A61B 5/263* (2021.01); *A61B 5/07* (2013.01); *A61B 5/277* (2021.01)

(58) Field of Classification Search
CPC .... A61B 5/263–268; A61B 5/277; A61B 5/07
See application file for complete search history.

(56) References Cited

U.S. PATENT DOCUMENTS 4,050,453 A * 9/1977 Castillo .................... A61B 5/25
600/391
4,777,954 A * 10/1988 Keusch .................... A61B 5/25
600/397
(Continued)

FOREIGN PATENT DOCUMENTS

CN 105852926 B * 3/2019 ....... A61B 17/12013
JP 2015506913 A 3/2015
(Continued)

OTHER PUBLICATIONS

Sun, Bao-feng, Translation of CN-105852926-B, 2019 (Year: 2019).*
(Continued)

*Primary Examiner* — Adam Z Minchella
(74) *Attorney, Agent, or Firm* — Slater Matsil, LLP

(57) ABSTRACT

An embodiment includes a bioelectrode including a hydrogel film, a conductive film, and a protective film. The conductive film is formed on one surface of the hydrogel film, and the protective film is formed on the other surface of the hydrogel film. The hydrogel film is comprises a mixture of a first material and a second material and is compatible with a living body, the first material configured to cause a sol-gel change at a temperature within a predetermined range around a body temperature of the living body and being compatible with the living body, the second material configured to not cause a sol-gel change at the temperature and being compatible with the living body. The protective film is provided to suppress the infiltration of water into the hydrogel film. The protective film can be made of a waterproof material or a water-repellent material.

4 Claims, 21 Drawing Sheets

(56)        References Cited

U.S. PATENT DOCUMENTS

| 2009/0005667 | A1 * | 1/2009 | Cui | A61N 1/0472 |
| | | | | 600/395 |
| 2010/0298668 | A1 | 11/2010 | Hafezi et al. | |
| 2012/0300370 | A1 * | 11/2012 | Chacko | H01G 9/028 |
| | | | | 427/79 |
| 2013/0129869 | A1 | 5/2013 | Hafezi et al. | |
| 2015/0276430 | A1 * | 10/2015 | Sekitani | G06F 3/0445 |
| | | | | 324/609 |

FOREIGN PATENT DOCUMENTS

| JP | 2015142754 A | 8/2015 | | |
| WO | WO-2013028548 A2 * | 2/2013 | ......... | A61B 10/0045 |
| WO | WO-2014162341 A1 * | 10/2014 | ........... | A61B 5/0537 |

OTHER PUBLICATIONS

Honda, Kei, Translation of WO-201462341-A1, 2014 (Year: 2014).*

Keller, A. et al., "Conducting hydrogels for edible electrodes," Journal of Materials Chemistry B, Royal Society of Chemistry, Jun. 12, 2017, 11 pages.

Xu, W. et al., "Food-Based Edible and Nutritive Electronics," Communication, Advanced Materials Technologies, Jul. 10, 2017, 7 pages.

* cited by examiner

BIOELECTRODE AND CAPACITOR

CROSS-REFERENCE TO RELATED APPLICATIONS

This patent application is a national phase filing under section 371 of PCT/JP2020/046941, filed Dec. 16, 2020, which is incorporated herein by reference in its entirety.

TECHNICAL FIELD

The present invention relates to a bioelectrode and a capacitor using biocompatible materials.

BACKGROUND

Examples of capacitors using biocompatible materials include NPL 1 and NPL 2. These studies are intended to change the capacitance depending on the pressure and pH in the body, and can be used for estimating the state in the body by forming an RLC circuit in combination with an antenna coil and reading a change in resonance frequency from the outside of the body by magnetic field coupling. The change in capacitance uses a change in dielectric constant between electrode plates or a distance between electrode plates, and a conductive material and a dielectric material are both constituted of a biocompatible material that is harmless to the body.

In addition, as an electrode that is a component of a capacitor, in the field of sensors to be attached to a body surface, there is PTL 1 using a gel, which proposes a two-layer structure of a conductive layer and a gel layer.

CITATION LIST

Patent Literature

[PTL 1] WO 2012/124216

Non Patent Literature

[NPL 1] A. Keller et al., "Conducting hydrogels for edible electrodes," Journal of Materials Chemistry B, vol. 5, pp. 5318-5328, 2017.
[NPL 2] W. Xu et al., "Food-Based Edible and Nutritive Electronics," Advanced Materials Technology, 1700181, 2017.

SUMMARY

Technical Problem

However, the technique described above has the following problems. Although a gel to which sugar or salt is added is used for the substrate of the electrode, in this configuration, when the gel is brought into contact with body fluids such as gastric juice to absorb moisture, there is a concern that the electrode will be broken due to swelling of the gel or the like. On the other hand, the use of a material which is too difficult to degrade in the body may affect the digestion process.

As a result, in the related art, there is a likelihood that a capacitor that operates properly in the body cannot be produced. For example, even for the purpose of collecting information at a specific place such as the stomach, small intestine, large intestine, etc., in the related art, the life of a capacitor cannot be controlled, and there occurs a case where the operation at a desired position cannot be guaranteed.

The embodiments of the present invention has been made to solve the problem described above and an object thereof is to make it possible to produce a capacitor that operates properly in the body.

Solution to Problem

A bioelectrode according to the embodiments of the present invention includes: a hydrogel film that is composed of a mixture of a first material and a second material and is compatible with a living body, the first material causing a sol-gel change at a temperature within a predetermined range around a body temperature of the living body and being compatible with the living body, the second material not causing a sol-gel change at the temperature and being compatible with the living body; a conductive film formed on one surface of the hydrogel film; and a protective film that is formed on the other surface of the hydrogel film and suppresses infiltration of water into the hydrogel film.

Further, a capacitor according to the embodiments of the present invention uses two bioelectrodes described above.

Advantageous Effects of Embodiments of the Invention

As described above, according to the embodiments of the present invention, since a protective film for suppressing infiltration of water into a hydrogel film is formed on the other surface of the hydrogel film composed of a mixture of a first material causing a sol-gel change at a temperature within a predetermined range around the body temperature of a living body and a second material not causing a sol-gel change at the temperature, a capacitor that operates properly in the body can be produced.

DETAILED DESCRIPTION OF ILLUSTRATIVE EMBODIMENTS

Figure 1:
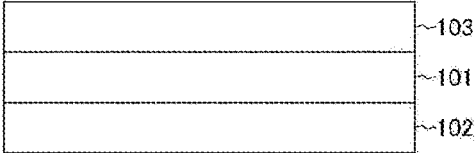
FIG. 1 is a configuration diagram illustrating a configuration of a bioelectrode according to an embodiment of the present invention.

Hereinafter, a bioelectrode according to an embodiment of the present invention will be described with reference to FIG. 1. The bioelectrode includes a hydrogel film 101, a conductive film 102, and a protective film 103. The conductive film 102 is formed on one surface of the hydrogel film 101, and the protective film 103 is formed on the other surface of the hydrogel film 101.

The hydrogel film 101 is composed of a mixture of a first material and a second material and is compatible with a living body, the first material causing a sol-gel change at a temperature within a predetermined range around a body temperature of the living body and being compatible with the living body, the second material not causing a sol-gel change at the temperature and being compatible with the living body. The first material can be gelatin, and the second material may be chitosan. Also, the first material can be a material having a melting point near a body temperature, such as butter, cacao butter, shea butter, coconut oil, or the like. The second material can also be a material with a slightly higher melting point, such as agar.

The conductive film 102 can be, for example, a film (metal film) made of a metal such as Au. The conductive film 102 can also be made of a conductive polymer material.

The protective film 103 is provided to suppress the infiltration of water into the hydrogel film 101. The protective film 103 can be made of a waterproof material or a water-repellent material. The protective film 103 can be, for example, an insolubilized film made of sodium alginate and calcium chloride or a water-repellent film made of beeswax.

Since the bioelectrode uses, as a support, the hydrogel film 101 formed by mixing a first material causing a sol-gel change near a body temperature and a second material not causing a sol-gel change, a disintegration time in the body can be controlled. In addition, since the hydrogel film 101 made of gelatin and chitosan has adhesive force, the conductive film 102 made of an Au film formed on another substrate (glass substrate) by a sputtering method or the like can be easily transferred onto the hydrogel film 101, and thus the bioelectrode can be easily produced.

Here, the hydrogel film 101 alone swells and easily disintegrates by absorbing moisture in the body, for example. For this reason, in the embodiment, the protective film 103 is formed to overlap the hydrogel film 101 to suppress the absorption of water and control the time required for the disintegration of the hydrogel film 101.

According to the embodiment, the bioelectrode can be prevented from immediately disintegrating in the body. Further, according to the embodiment, the bioelectrode can be brought into a state of gradually disintegrating due to temperature.

Figure 2A:
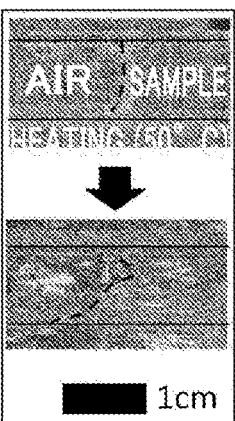
FIG. 2A is an explanatory diagram illustrating a temperature change in an actually produced hydrogel film 101.
Figure 2B:
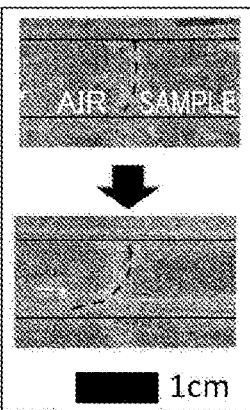
FIG. 2B is an explanatory diagram illustrating a temperature change in the actually produced hydrogel film 101.
Figure 2C:
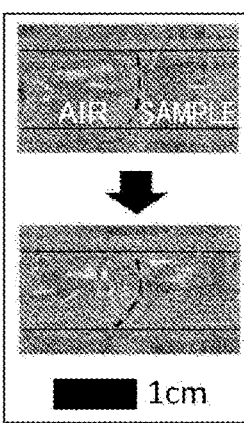
FIG. 2C is an explanatory diagram illustrating a temperature change in the actually produced hydrogel film 101.
Figure 2D:
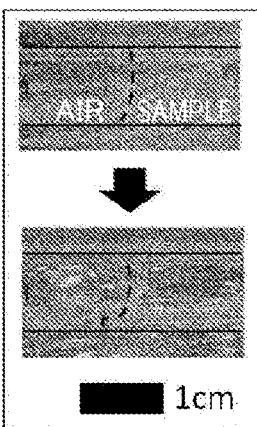
FIG. 2D is an explanatory diagram illustrating a temperature change in the actually produced hydrogel film 101.
Figure 2E:
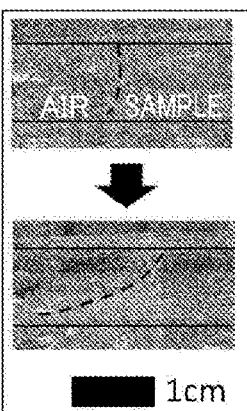
FIG. 2E is an explanatory diagram illustrating a temperature change in the actually produced hydrogel film 101.

Next, a temperature change in the actually produced hydrogel film 101 will be described with reference to FIGS. 2A, 2B, 2C, 2D, and 2E. FIG. 2A shows the result of observing the state of an aqueous solution of 25 wt % of gelatin that was filled in a rectangular parallelepiped cell, solidified at room temperature, and then rolled on its side, while being heated at the lower part to 50° C. for 1 minute. FIG. 2B shows the result of observing the state of an aqueous solution of 1 wt % of chitosan and 24 wt % of gelatin that was filled in a rectangular parallelepiped cell, solidified at room temperature, and then rolled on its side, while being heated at the lower part to 50° C. for 1 minute. FIG. 2C shows the result of observing the state an aqueous solution of 2 wt % of chitosan and 23 wt % of gelatin filled in a rectangular parallelepiped cell that was solidified at room temperature, and then rolled on its side, while being heated at the lower part to 50° C. for 1 minute. FIG. 2D shows the result of observing the state of an aqueous solution of 3 wt % of chitosan and 22 wt % of gelatin that was filled in a rectangular parallelepiped cell, solidified at room temperature, and then rolled on its side, while being heated at the lower part to 50° C. for 1 minute. FIG. 2E shows the result of observing the state of an aqueous solution of 1 wt % of chitosan that was filled in a rectangular parallelepiped cell, solidified at room temperature, and then rolled on its side, while being heated at the lower part to 50° C. for 1 minute.

Gelatin changes from gel to sol with heating, and chitosan originally flows out as a solution, whereas the liquefaction delay is observed by mixing gelatin and chitosan. In addition, in FIGS. 2A, 2B, 2C, 2D, and 2E, the dotted line in the drawing is the boundary line between the air and the sample. From these results, it can be said that the time of change from gel to sol can be controlled through the mixing ratio of gelatin and chitosan.

Figure 3A:
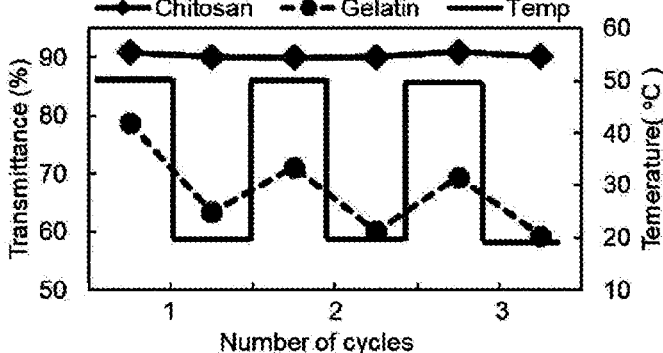
FIG. 3A is an explanatory diagram illustrating a relationship between a temperature and the hydrogel film 101.
Figure 3B:
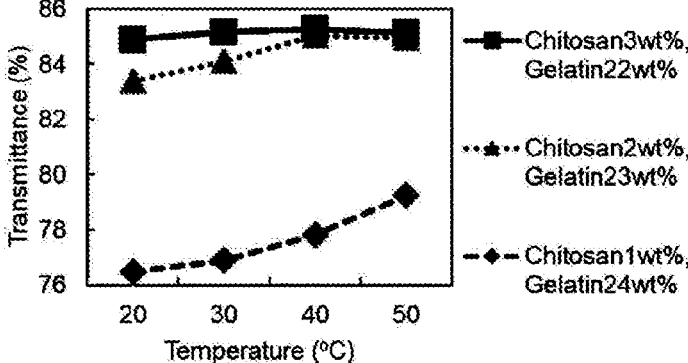
FIG. 3B is an explanatory diagram illustrating a relationship between a temperature and the hydrogel film 101.

Next, the relationship between the temperature and the hydrogel film 101 will be described. As illustrated in FIGS. 3A and 3B, the sol-gel change of gelatin can be quantitatively observed as a change in transmittance (wavelength of 550 nm) due to temperature, but chitosan does not change. It can also be seen that the change in transmittance with temperature changes depending on the combination ratio of gelatin and chitosan. For example, when chitosan is 2 wt % and gelatin is 23 wt %, and when chitosan is 1 wt % and gelatin is 24 wt %, the ratio of gelatin is large and the change in gel/sol can be followed.

Figure 4A:
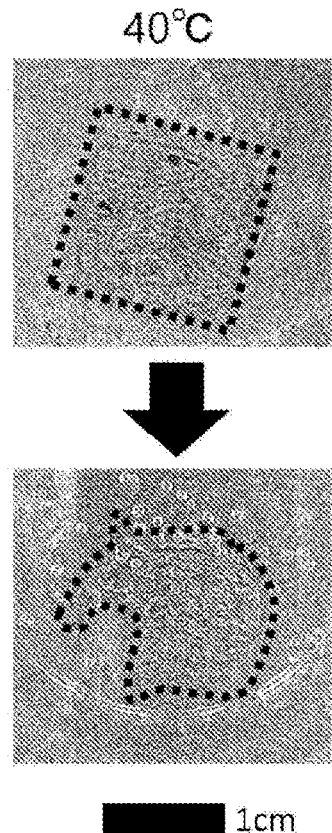
FIG. 4A is a photograph showing a change in a bioelectrode submerged in water at 40° C.
Figure 4B:
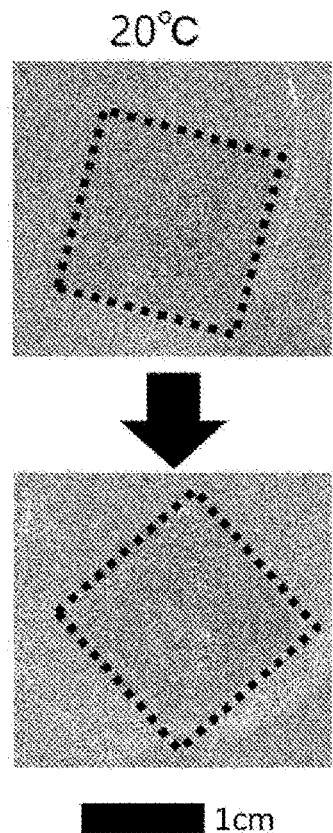
FIG. 4B is a photograph showing a change in a bioelectrode submerged in water at 20° C.

Next, the results of the experiment on the disintegration of the hydrogel film will be described with reference to FIGS. 4A and 4B. In the experiment, a bioelectrode composed of two layers of a hydrogel film and a conductive film was used. FIG. 4A shows a change in a bioelectrode submerged in water at 40° C. FIG. 4B also shows a change in a bioelectrode submerged in water at 20° C. As shown in FIG. 4A, at 40° C., the hydrogel film disintegrated into pieces due to solification, and the bioelectrode did not retain its initial structure.

Figure 5:
FIG. 5 is a photograph of an actually produced bioelectrode.

Next, an actually produced bioelectrode will be described with reference to FIG. 5. The bioelectrode is formed by transferring a gold film onto a hydrogel film made of gelatin and chitosan. Since the hydrogel film has flexibility, the hydrogel film is easily peeled from the glass plate on which the Au film is formed during transfer, and the patterned Au film can also be transferred.

Figure 6:
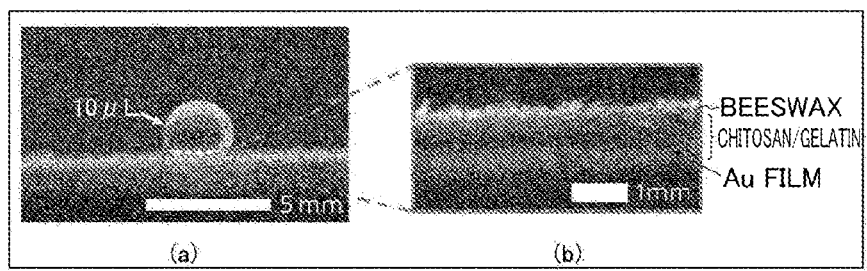
FIG. 6 is a photograph showing a water repellent state of a protective film.

Next, the protective film will be described with reference to FIG. 6. In addition, (b) of FIG. 6 enlarges a part of (a) of FIG. 6. Further, (a) of FIG. 6 shows a water droplet of 10 μL. FIG. 6 shows a cross-sectional view when a super water-repellent structure made of beeswax is produced as an example of a protective film for suppressing the absorption of water. Thus, the surface of the hydrogel film is subjected to the water-repellent treatment, whereby the absorption of water in the hydrogel film can be suppressed and the swelling of the hydrogel film can be prevented (delayed).

When there is no protective film, the hydrogel film absorbs a large amount of water. On the other hand, when the insolubilized film is formed as a protective film, the degree of water absorption in the hydrogel film can be suppressed to some extent. When a water-repellent material or a super water-repellent material is formed as a protective film, there is an effect of greatly suppressing absorption of honey in the hydrogel film. By utilizing such a protective film, breakage of the bioelectrode due to swelling of the hydrogel film is suppressed.

Further, the protective film can be formed only on the other surface of the hydrogel film, and the protective film can also be formed on the surface of the conductive film formed on one surface of the hydrogel film. For example, by constituting the conductive film from a conductive polymer, when the conductive film absorbs water, when cracks or the like occur in the conductive film, or when one surface of the hydrogel film is partially exposed by patterning the conductive film, it is important to form a protective film also on the surface of the conductive film. Here, when the surface of the conductive film is desired to be exposed, a protective film is formed only in a gap such as between patterns or cracks. For example, a film of a material to be a protective film can be formed only in the above-mentioned gap by applying with a spotter or applying utilizing surface charge of a hydrogel film.

Figure 7A:
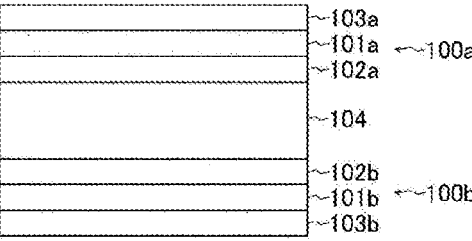
FIG. 7A is a configuration diagram illustrating a configuration of a capacitor according to an embodiment of the present invention.
Figure 7B:
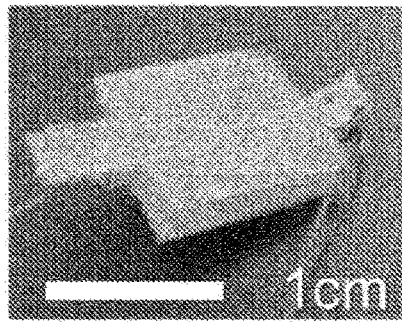
FIG. 7B is a photograph showing the appearance of an actually produced capacitor.

Next, a capacitor according to an embodiment of the present invention will be described with reference to FIGS. 7A and 7B. This capacitor is constituted using two bioelectrodes described above. The capacitor can be formed by disposing the two bioelectrodes to be spaced apart from each other. For example, a first bioelectrode 100a and a second bioelectrode 100b are disposed with a first conductive film 102a and a second conductive film 102b facing each other. Note that the first conductive film 102a is formed on one surface of a hydrogel film 101a, and a protective film 103a is formed on the other surface of the hydrogel film 101a. In addition, the second conductive film 102b is formed on one surface of a hydrogel film 101b, and a protective film 103b is formed on the other surface of the hydrogel film 101b. In addition, a film 104 made of an external stimulus responsive substance, such as a polymer film made of sodium polyacrylate, is disposed between the first bioelectrode 100a and the second bioelectrode 100b, thereby changing the interval between the first bioelectrode 100a and the second bioelectrode 100b and changing the capacitance.

Sodium polyacrylate is a polymer material having a volume change different depending on the position in the body due to the difference in osmotic pressure between gastric juice and water. Therefore, a dielectric constant and a thickness of the film 104 change depending on the position in the body, and the capacitance of the capacitor can be changed. FIG. 7B shows the appearance of a capacitor actually produced using sodium polyacrylate (20 wt %) as the film 104.

Figure 8A:
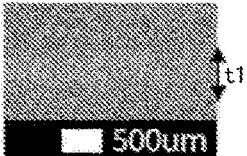
FIG. 8A is a cross-sectional photograph showing a state of a polymer film disposed between two bioelectrodes constituting a capacitor.
Figure 8B:
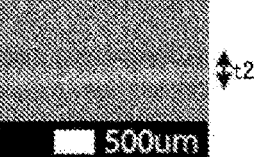
FIG. 8B is a cross-sectional photograph showing a state of a polymer film disposed between two bioelectrodes constituting a capacitor.
Figure 8C:
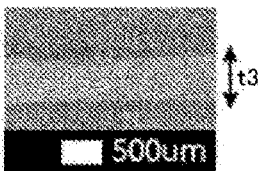
FIG. 8C is a cross-sectional photograph showing a state of a polymer film disposed between two bioelectrodes constituting a capacitor.

Here, as shown in FIGS. 8A, 8B, and 8C, thicknesses (t1, t2, and t3) of the polymer film disposed between the two bioelectrodes described above change depending on the environment. The thickness t1 (FIG. 8A) of the polymer film in the initial capacitor produced is reduced to a thickness t2 (FIG. 8B) when the capacitor is immersed in the artificial gastric juice. On the other hand, when the capacitor is immersed in pure water, the polymer film becomes thicker than the thickness t3 (FIG. 8C).

Figure 9A:
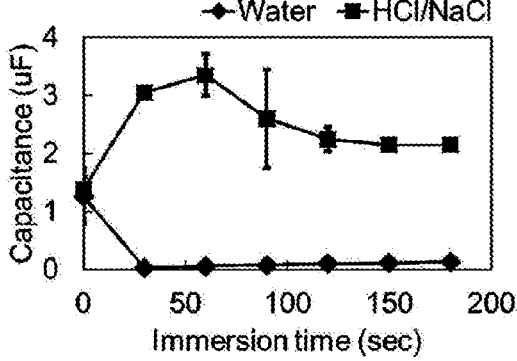
FIG. 9A is a characteristic diagram illustrating an example of measurement results obtained using the capacitor according to the embodiment.
Figure 9B:
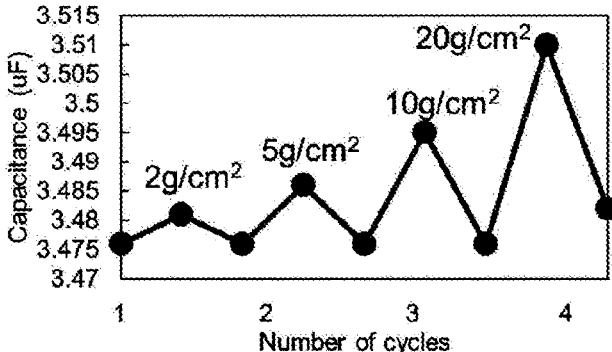
FIG. 9B is a characteristic diagram illustrating an example of measurement results obtained using the capacitor according to the embodiment.

Next, a measurement example using the capacitor described above will be described with reference to FIGS. 9A and 9B. At a measurement frequency of 1 kHz, a change in capacitance due to a difference between gastric juice and water and a change in capacitance due to a change in pressure applied to the capacitor are shown. Since the capacitance measurement is performed at a low frequency, the value contains the capacitance of the solution containing the polarization of water and ions. It can be seen that after the pressure is applied, the distance between the two bioelectrodes is changed by the restoration of the polymer film, and the capacitance approaches the original value.

Incidentally, in the capacitor, a large difference in dielectric constant between air (gas) and water can be utilized when a capacitance change is generated from a change in dielectric constant between two bioelectrodes without changing the interval between the two bioelectrodes. For example, the capacitance when an air layer having a thickness of 99 μm and a polymer film having a thickness of 1 μm are disposed between two bioelectrodes is set to $C_0$. Further, the capacitance when an air layer having a thickness of 90 μm and a polymer film having a thickness of 10 μm are disposed between two bioelectrodes is set to $C_1$. Further, the capacitance when a polymer film having a thickness of 100 μm is disposed between two bioelectrodes is set to $C_2$.

When communication is performed around 13.56 MHz by magnetic field coupling, if the inductance is about 6 μH, the capacitance of the capacitor should be about C=1-100 pF. Assuming that the area of the facing surfaces of the two bioelectrodes is 1 cm$^2$, the interval between the two bioelectrodes is about 100 μm. However, when the self-resonant frequency is exceeded at a high frequency, the capacitor is going to act as an inductor, and therefore, it is necessary to perform impedance measurement and select a frequency within a range that functions as a capacitor. That is, the design value is an example, and is not limited to 13.56 MHz.

The capacitances $C_0$, $C_1$, and $C_2$ described above are represented by the following Equations (1) to (3) by series connection.

[Math. 1]

$$C_0 = \frac{\varepsilon_0 S}{a_0/\varepsilon_{gel} + b_0/\varepsilon_{air}} \tag{1}$$

$$\frac{C_1}{C_0} = \frac{a_0/\varepsilon_{gel} + b_0/\varepsilon_{air}}{(a_1)/\varepsilon_{gel'} + (b_1)/(\varepsilon_{air})} \tag{2}$$

$$\frac{C_2}{C_0} = \frac{a_0/\varepsilon_{gel} + b_0/\varepsilon_{air}}{(a_2)/\varepsilon_{gel''}} \tag{3}$$

7

-continued $$\frac{C_1}{C_0} = \frac{1 \times 10^{-6}/5 + 99 \times 10^{-6}/1}{(10 \times 10^{-6})/69.5 + (90 \times 10^{-6})/1} = 1.1 \quad (4)$$

$$\frac{C_2}{C_0} = \frac{1 \times 10^{-6}/5 + 99 \times 10^{-6}/1}{(100 \times 10^{-6})/80} = 79.3 \quad (5)$$

Assuming that a dielectric constant $\varepsilon_{gel}$ of the polymer film is 5 and a dielectric constant of water is 80, when the dielectric constant of the mixture of air and the polymer film is calculated from the ratio according to the Maxwell-Garnett model, the change in capacitance from the capacitance $C_0$ is slightly less than 100-fold different in gastric juice and water using approximately $\varepsilon_{gel}=5$, $\varepsilon_{gel}'=69.5$, and $\varepsilon g_{el}''=80$. This can be read as a change in resonance frequency.

Figure 10:
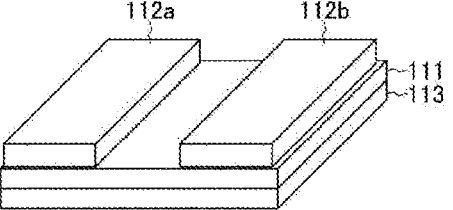
FIG. 10 is a perspective view illustrating a configuration of another capacitor according to the embodiment.

Next, another capacitor according to the embodiment will be described with reference to FIG. 10. In the capacitor, the two bioelectrodes are composed of two conductive films 112a and 112b disposed to be spaced apart from each other on the hydrogel film 111 using the hydrogel film 111 in common. A protective film 113 is formed on the rear surface side of the hydrogel film 111. By disposing the two conductive films 112a and 112b constituting the two bioelectrodes to be spaced apart from each other on the hydrogel film 111, a capacitor can be formed.

Figure 11:
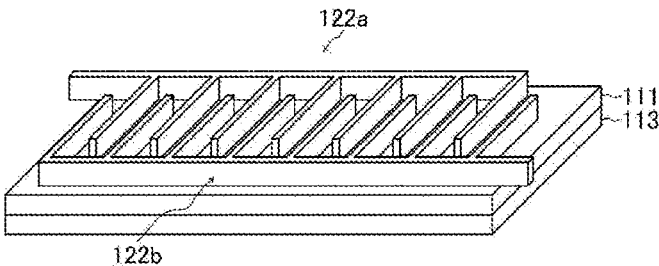
FIG. 11 is a perspective view illustrating a configuration of another capacitor according to the embodiment.

Here, if the capacitance is about 1-100 pF and the area of the facing surfaces of the conductive films 112a and 112b is about 1 cm², the distance between the conductive films 112a and 112b is 50×10⁻⁹ m, and the thicknesses of the conductive films 112a and 112b are set to about 1 μm. On the other hand, as illustrated in FIG. 11, when two conductive films 122a and 122b are formed in a comb-tooth shape, and comb teeth are disposed to be alternately inserted, a practical distance between the two conductive films and a thickness of the conductive films can be designed.

For example, if the number of comb teeth is 500, it is necessary to consider the parasitic capacitance, but the distance between the two conductive films can be 2.5 μm, the thickness of the conductive films can be 100 nm, and the length of the overlapping comb teeth can be 1 cm. The capacitor having this configuration can also be detected as a change in capacitance by changing the dielectric constant between the two conductive films as described above. In addition, as compared with the above-described capacitor, since the capacitor illustrated in FIGS. 10 and 11 has a structure in which the two conductive films can be brought into direct contact with an external liquid. Therefore, although it is necessary to consider breakage of the capacitor due to swelling of the hydrogel film, it can be expected that the reaction time will be shortened.

As described above, according to the embodiments of the present invention, since a protective film for suppressing infiltration of water into a hydrogel film is formed on the other surface of the hydrogel film composed of a mixture of a first material causing a sol-gel change at a temperature within a predetermined range around the body temperature of a living body and a second material not causing a sol-gel change at the temperature, a capacitor that operates properly in the body can be produced.

According to the embodiments of the present invention, the disintegration time in the body can be controlled by using a hydrogel film in which a material causing a sol-gel change near the body temperature and a material not causing a sol-gel change are mixed. Further, the absorption of water can be suppressed by overlapping the protective film. As a result, the bioelectrode can be made to be a material which is not immediately disintegrated and is gradually disintegrated due to temperature, and a capacitor can be produced by using the bioelectrode.

The capacitor according to the embodiments of the present invention forms an RLC circuit in combination with an antenna coil, so that a change in resonance frequency can be read from the outside of the body by magnetic field coupling, and a state in the body can be estimated. Since the application destination of the embodiments of the present invention is not limited to the body but uses a biodegradable material, the present invention can also be used for measurements in water (by selecting a hydrogel film that responds to external stimuli and measuring ions, pH, and the like in environments such as water quality surveys, hydroponics, and aquaculture).

Also, it is apparent that the present invention is not limited to the embodiment described above, and many modifications and combinations can be carried out by those having ordinary knowledge in the art within the technical idea of the present invention.

REFERENCE SIGNS LIST

101 Hydrogel film
102 Conductive film
103 Protective film

The invention claimed is:

1. A capacitor comprising:
a pair of bioelectrodes, each of the pair of bioelectrodes comprising:
a hydrogel film comprising a mixture of a first material and a second material, the first material configured to cause a sol-gel change at a temperature within a predetermined range around a body temperature of a living body and being compatible with the living body, the second material configured to not cause a sol-gel change at the temperature and being compatible with the living body;
a conductive film formed on one of surfaces of the hydrogel film; and
a protective film formed on the other one of the surfaces of the hydrogel film and configured to suppress infiltration of water into the hydrogel film, and
a polymer film disposed between the pair of bioelectrodes, wherein the pair of bioelectrodes are arranged with the conductive films facing each other.

2. The capacitor according to claim 1, wherein the polymer film comprises sodium polyacrylate.

3. A bioelectrode comprising:
a hydrogel film comprising a mixture of a first material and a second material, the first material configured to cause a sol-gel change at a temperature within a predetermined range around a body temperature of a living body and being compatible with the living body, the second material configured to not cause a sol-gel change at the temperature and being compatible with the living body;
a protective film formed on a first surface of the hydrogel film and configured to suppress infiltration of water into the hydrogel film, and
two conductive films disposed apart from each other on a second surface of the hydrogel film.

4. The bioelectrode according to claim 3, wherein each of the two conductive films is formed in a comb-tooth shape having comb teeth, and the comb teeth of the two conductive films are disposed to be alternately inserted.

\*  \*  \*  \*  \*